United States Patent
Ives et al.

(10) Patent No.: US 6,266,556 B1
(45) Date of Patent: *Jul. 24, 2001

(54) METHOD AND APPARATUS FOR RECORDING AN ELECTROENCEPHALOGRAM DURING TRANSCRANIAL MAGNETIC STIMULATION

(75) Inventors: John R. Ives, Lexington; Alvaro Pascual-Leone, Wayland, both of MA (US)

(73) Assignee: Beth Israel Deaconess Medical Center, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/067,111

(22) Filed: Apr. 27, 1998

(51) Int. Cl.⁷ .............................. A61B 5/04; A61B 17/52; A61N 1/00

(52) U.S. Cl. ............................... 600/544; 600/9; 600/13; 600/14; 600/15

(58) Field of Search ................................. 600/544, 300, 600/547, 9, 13, 14, 15

(56) References Cited

U.S. PATENT DOCUMENTS

| | | |
|---|---|---|
| 2,998,433 | 8/1961 | Schaub et al. . |
| 3,047,468 | 7/1962 | Origoni et al. . |
| 3,928,326 | 12/1975 | Brattsand et al. . |
| 4,033,334 | 7/1977 | Fletcher et al. .................. 128/2.1 E |

(List continued on next page.)

FOREIGN PATENT DOCUMENTS

| | | | |
|---|---|---|---|
| 28 31 099 | 1/1980 | (DE) | .............................. A61B/5/04 |
| 0164636 | 12/1985 | (EP) . | |
| 0262108 | 3/1988 | (EP) . | |
| 0508900 | 10/1992 | (EP) . | |
| 1429922 | 3/1976 | (GB) . | |

(List continued on next page.)

OTHER PUBLICATIONS

International Search Report from International Patent Application PCT/US99/13051, filed Jun. 9, 1999.

Bohning, D: "Interleaved Transcranial Magnetic Stimulation (TMS) and fMRI", proceedings of the international society for magnetic resonance in medicine, Sixth Scientific Meeting and Exhibition, Sydney, Australia, Apr. 18–24, 1998, vol. 1, p. 508.

Bohning, D: "Echoplanar BOLD fMRI of Brain Activation Induced by Concurrent Transcranial Magnetic Stimulation", Investigative Radiology, vol. 33, No. 6, Jun. 1998, pp. 336–340.

(List continued on next page.)

Primary Examiner—Cary O'Connor
Assistant Examiner—Navin Natnithithadha
(74) Attorney, Agent, or Firm—Wolf, Greenfield & Sacks, P.C.

(57) ABSTRACT

A system for monitoring an electroencephalogram of a patient during administration of transcranial magnetic stimulation including a transcranial magnetic stimulation (TMS) system, an electroencephalogram (EEG) monitoring system, and a control system, coupled between the EEG system and the TMS system, that responds to signals provided by the EEG system and controls the TMS system wherein timing of operation of the TMS system does not need to be synchronized to timing of operation of the EEG system. A conductive plastic electrode system for use with the EEG monitoring system is also provided.

15 Claims, 5 Drawing Sheets

U.S. PATENT DOCUMENTS

| | | |
|---|---|---|
| 4,736,751 | 4/1988 | Gevins et al. . |
| 4,944,015 | 7/1990 | Juve et al. . |
| 4,949,725 | 8/1990 | Raviv et al. . |
| 4,951,674 | 8/1990 | Zanakis et al. . |
| 4,974,602 | 12/1990 | Abraham-Fuchs et al. . |
| 4,994,015 | 2/1991 | Cadwell . |
| 5,119,816 | 6/1992 | Gevins . |
| 5,159,929 | 11/1992 | Morris et al. . |
| 5,217,010 | 6/1993 | Tsitlik et al. . |
| 5,220,921 | 6/1993 | Ferris et al. . |
| 5,269,315 | 12/1993 | Leuchter et al. . |
| 5,323,776 | 6/1994 | Blakeley et al. . |
| 5,445,162 | 8/1995 | Ives . |
| 5,707,334 | 1/1998 | Young .................................. 600/9 |
| 5,769,778 * | 6/1998 | Abrams et al. ..................... 600/14 |
| 5,794,620 | 8/1998 | Dossel et al. . |
| 5,833,600 | 11/1998 | Young . |

FOREIGN PATENT DOCUMENTS

| | | |
|---|---|---|
| 1469575 | 4/1977 | (GB) . |
| 2 307 411 | 5/1997 | (GB) ............................ A61B/5/04 |
| 9104984 | 4/1991 | (WO) . |
| WO 92/21281 | 12/1992 | (WO) ............................ A61B/5/00 |
| WO94/12099 | 6/1994 | (WO) ............................ A61B/5/04 |
| WO98/18384 | 5/1998 | (WO) ............................ A61B/5/04 |

OTHER PUBLICATIONS

Bohning, D: "Mapping transcranial magnetic stimulation (TMS) fields in vivo with MRI", Neuroreport, vol. 8, No. 11, 1997, pp. 2535–2538.

Pascual–Leone, A, et al.: "Effects of Repetitive Transcranial Magnetic Stimulation (rTMS) on Motor Cortex Activity During a Rate Controlled Motor Task as Measured by Functional Magnetic Resonance Imaging (fMRI)", Neurology, vol. 48, No. 3, (supp. 2), 1997, p. A106.

International Search Report from International Patent Application No. PCT/US99/08489, filed Apr. 22, 1999.

Ilmoniemi RJ, Virtanen J: "Neuronal Responses To Magnetic Stimulation Reveal Cortical Reactivity and Connectivity" NEUROREPORT, vol. 8, No. 16, Nov. 10, 1997, pp. 3537–3540.

Ruohonen J: "Transcranial Magnetic Stimulation: Modelling and New Techniques" Dissertation, Department of Engineering Physics and Mathematics Laboratory Of Biomedical Engineering Helsinki University Of Technology, Dec. 4, 1998, p. 28, paragraph 2—p.30, paragraph 1; figure 6.

* cited by examiner

METHOD AND APPARATUS FOR RECORDING AN ELECTROENCEPHALOGRAM DURING TRANSCRANIAL MAGNETIC STIMULATION

BACKGROUND OF THE INVENTION

1. Field of the Invention

The present invention relates to medical diagnostic and treatment methods and apparatus.

2. Discussion of the Related Art

An electroencephalogram (EEG) is a record of specific brain wave patterns in a patient. EEG systems permit the recording of the brain wave patterns. An EEG system typically includes a plurality of conductive electrodes that are placed on a patient's scalp. These electrodes are typically metal and are connected to a preamplifier that processes the signals detected by the electrodes and provides amplified signals to an EEG machine. The EEG machine contains hardware and software that interprets the signals to provide a visual display of the brain wave activity detected by the electrodes. This brain wave activity is typically displayed on a strip chart recorder or computer monitor.

Transcranial magnetic stimulation (TMS) is a technique for stimulating the human brain non-invasively. TMS uses the principle of inductance to get electrical energy across the scalp and skull without the pain of direct percutaneous electrical stimulation. It involves placing a coil of wire on the scalp and passing a powerful and rapidly changing current through it. This produces a magnetic field which passes unimpeded and relatively painlessly through the tissues of the head. The peak strength of the magnetic field is related to the magnitude of the current and the number of turns of wire in the coil. This magnetic field, in turn, induces a much weaker electrical current in the brain. The strength of the induced current is a function of the rate of change of the magnetic field, which is determined by the rate of change of the current in the coil. In order to induce enough current to depolarize neurons in the brain, the current passed through the stimulating coil must start and stop or reverse its direction within a few hundred microseconds.

TMS is currently used in several different forms. In a first form, called single-pulse TMS, a single pulse of magnetic energy is delivered from the coil to the patient. Repetitive TMS or rTMS, refers to the delivery of a train of pulses delivered over a particular time period. An example of rTMS could be a train of pulses having a 10 Hz repetition rate that lasts for approximately 8 to 10 seconds. In a typical application, this train of pulses is repeated every 30 seconds for up to 20 or 30 minutes.

In order to monitor the safety and efficacy of a TMS application, it would be desirable to monitor a patient's EEG during a TMS session. However, monitoring a patient's EEG during a TMS pulse presents problems because at least the preamplifiers used in current EEG systems experience saturation caused by the magnetic field generated by the TMS system. Since the electrodes used to monitor the EEG are typically in close proximity to the TMS coil, the magnetic pulse induces a signal in one or more of the EEG electrodes which causes the EEG preamplifiers to saturate. Typical preamplifiers used in EEG systems take a relatively long time to recover after being saturated by a TMS pulse.

One currently available EEG system has preamplifiers that recover, i.e., return to normal operation, after 150 milliseconds after the TMS pulse has ended. This presents a problem since, in a typical TMS pulse train, the time interval between pulses is approximately 100 milliseconds. If the amplifiers come out of saturation after 150 milliseconds, the next TMS pulse has already resaturated the amplifier and therefore it is simply not possible to record or observe the EEG during a typical TMS pulse train.

Another system for monitoring EEG during TMS includes amplifiers in the EEG system that use a sample-and-hold circuit to pin the amplifier to a constant level during the TMS pulse. The amplifiers are said to recover within 100 microseconds after the end of the TMS pulse. Although this system appears to allow monitoring of the EEG within a short time after the end of a TMS pulse, additional gating and synchronizing circuitry is necessary to control the operation of the EEG amplifiers with respect to the TMS system. Additional gating and sampling circuitry is undesirable because it requires additional circuitry and because it can be complicated.

An additional complication that occurs when a patient's EEG is monitored during TMS occurs because of the use of metal electrodes to sense EEG signals. Large eddy currents induced by the TMS pulse or pulses in the metal electrodes can cause localized heating that may result in burns to a patient's scalp. This presents a safety hazard.

Therefore, it would be desirable to provide a system that allows a patient's EEG to be monitored during a TMS pulse that overcomes at least these problems.

SUMMARY OF THE INVENTION

In broad terms, one aspect of the present invention provides a method and apparatus for monitoring a patient's EEG during TMS that does not require a time synchronization of the operation of the TMS device and the EEG system.

This aspect of the invention is provided by a system for monitoring an electroencephalogram of a patient during administration of transcranial magnetic stimulation, including a transcranial magnetic stimulation (TMS) device and an electroencephalogram (EEG) monitoring system. The system also includes a control system, coupled between the EEG system and the TMS device, that responds to signals provided by the EEG system and controls the TMS device, wherein timing of operation of the TMS device does not need to be synchronized to timing of operation of the EEG system.

In accordance with another aspect of the invention, an electrode system that may be used to detect EEG signals that does not experience heating as a result of the TMS pulse so as to avoid burning a patient's scalp is provided. The electrode system includes an electrically conductive plastic electrode, a wire molded into a surface of the conductive plastic electrode, and a coating of conductive epoxy disposed on the surface of the conductive plastic electrode.

BRIEF DESCRIPTION OF THE DRAWINGS

In the drawings, which are incorporated herein by reference and in which like elements have been given like reference characters.

DETAILED DESCRIPTION

Figure 1:
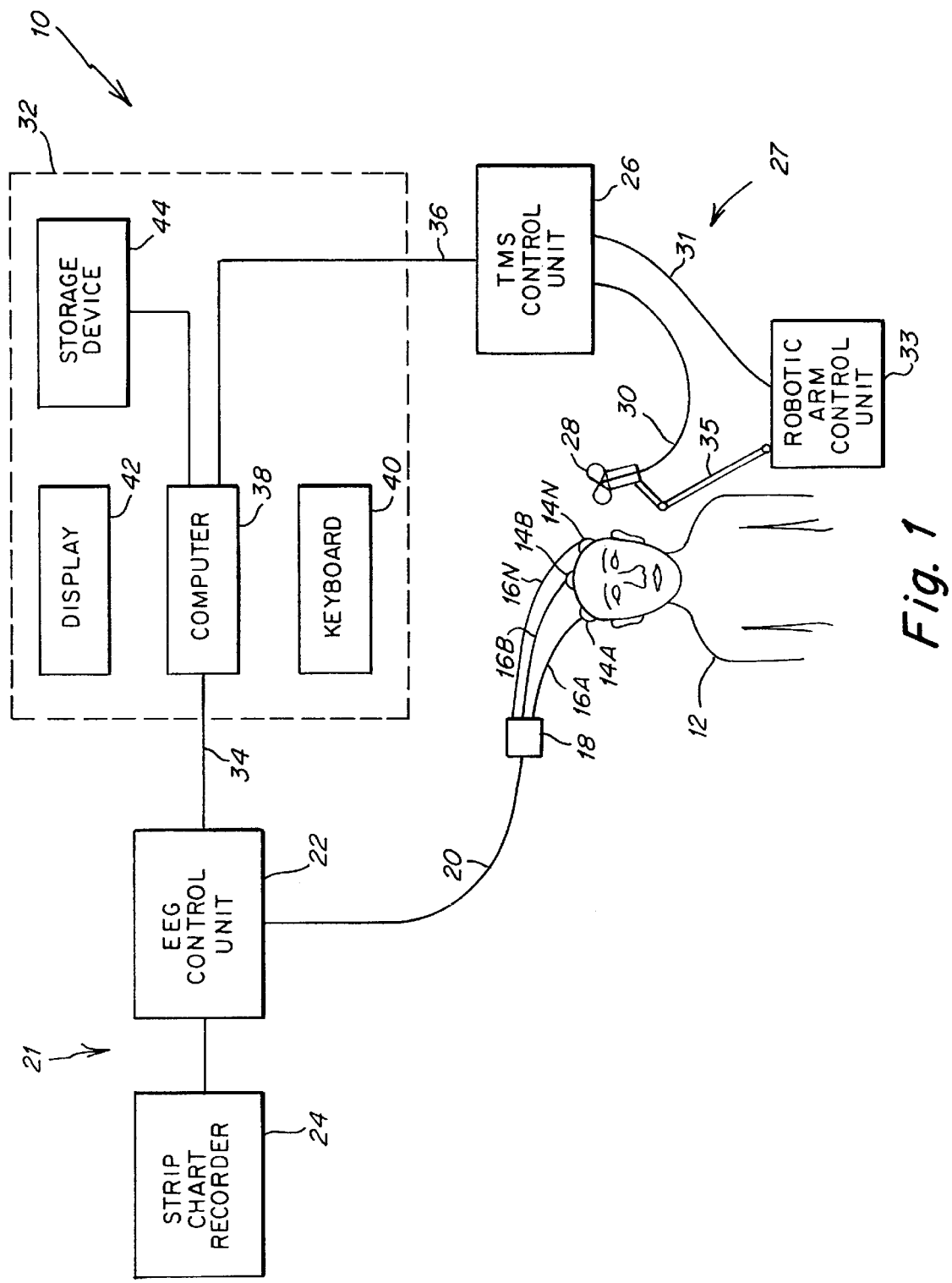
FIG. 1 is an overall schematic block diagram of the system of the present invention.

Reference is now made to FIG. 1, which figure illustrates an overall block diagram of the present invention. The invention includes an EEG system 21, a TMS system 27, and a control system 32 coupled between EEG system 21 and TMS system 27. As will be explained, control system 32 responds to EEG signals provided by EEG system 21 and controls TMS system 27. EEG system 21 and TMS system 27 may be of any number of commercially available systems.

A patient 12 has a number of electrodes 14a, 14b, ... 14n attached to his or her scalp in a conventional manner. Electrodes 14a–14n are used to sense brain activity to provide an EEG. The electrical brain activity sensed by electrodes 14a–14n is converted into an electrical signal that is transmitted over wires 16a, 16b, ... 16n to preamplifier 18. The electrodes 14a–14n may be located on the patient's scalp in accordance with the international 10–20 system. In one embodiment of the invention, preamplifier 18 has 18 channels and 18 electrodes are used. However, one skilled in the art will appreciate that amplifier 18 can be provided with additional channels and additional electrodes can be provided. Preamplifier 18 is constructed and arranged to be small and lightweight and may be located so that it lies at the nape of the neck. As will be explained in more detail hereinafter, preamplifier 18 is constructed so that it is small and provides a relatively high gain close to the electrodes with a limited bandpass and relatively high common mode rejection ratio. Preamplifier 18 may use surface mount components. As will be explained in detail hereinafter, the use of this type of amplifier construction makes preamplifier 18 less susceptible to magnetically-induced artifacts caused by TMS pulses.

The output of preamplifier 18 is carried by conductor 20 to EEG control unit 22. EEG control unit 22 has appropriate processing circuitry for processing the signal received on conductor 20 to provide a visual indication or record of brain wave activity. A strip chart recorder 24 may also be provided to provide a paper record of the electroencephalogram.

A transcranial magnetic stimulation system 27 is also provided in the system. TMS system 27 includes a coil 28 coupled to TMS control unit 26 via conductor 30. TMS control unit 26 provides a high current short time duration signal to coil 28 via conductor 30 that causes coil 30 to generate a large magnetic pulse. If a series of current pulses are provided, then coil 28 will generate a series of magnetic pulses. Typically, coil 28 is held in close proximity to the patient's head in a region where magnetic stimulation is desired.

A control system 32 is provided between EEG system 21 and TMS system 27. As will be explained in more detail hereinafter, control system 32 receives the EEG signals provided by EEG system 21 on conductor 34 and uses those signals, either automatically or under control of an operator, to control TMS system 27 via conductor 36.

Control system 32 may include a computer 38 having a keyboard 40, a display 42, and a mass storage device 44 connected thereto. Display 42 can be, for example, a cathode ray tube or flat panel LCD display. Mass storage device 44 can be any kind of magnetic or optical medium mass storage device such as a disk drive or a tape drive. Mass storage device 44 may be used for storing programs to be executed by computer 38 and EEG information provided by EEG system 21 as well as TMS information provided by TMS system 27.

The overall function of control system 32 is to monitor the EEG signals provided on cable 34 and to control TMS system 27 in response to these signals.

Control system 32 provides, in one embodiment, a safety shutdown control. One problem that may occur with TMS, particularly repetitive TMS, is that the magnetic pulses can cause seizure activity in the brain of the patient undergoing the TMS treatment. In some cases, the patient can actually go into a full body seizure. To avoid a seizure, control system 32 is used to monitor the EEG signals on conductor 34 and to turn off TMS system 27 via conductor 36 by providing an off control signal if seizure activity is detected. Seizure activity can be detected in several ways. In one mode of operation, an operator can view the EEG results on display 42 and if the operator detects changes in the EEG morphology exhibiting recruitment or the onset of a seizure discharge, the operator can activate a "stop" button, for example, in control system 32 to shut off TMS system 27 before the seizure actually occurs. In another embodiment, the EEG signal can be analyzed by a spectral analysis program or a template matching program running on computer 38. Once again, if the operator notices abnormal activity, control system 32 can be used to shut down TMS system 27 before a seizure results. In another embodiment, conventionally available computer software that automatically detects the onset of seizures using specified criteria can be used automatically in a control program running on computer 38 or in conjunction with the operator to shut off TMS system 27. Such seizure detection software is available from, for example, Stellate, Inc.

In accordance with another aspect of the invention, control system 32 can be used to recognize when the brain has been placed in a desired state as a result of the TMS procedure or can be used to recognize when the brain has been removed from an undesired state by the TMS procedure. For example, TMS has been found to be useful in the treatment of schizophrenia and depression. In these disorders, the EEG of the patient exhibits particular abnormal characteristics that can be seen in the patient's EEG. Using the present invention, the patient's EEG can be monitored while TMS is being applied and when the patient's EEG no longer contains these abnormal characteristics, the procedure may be stopped. Thus, the present invention allows an operator to determine if and when a TMS procedure has been successful.

Alternatively, the present invention can be used to determine when a patient's EEG and resulting brain activity has reached a desired state. For example, if a normal EEG is the target for a particular patient, then the present invention may be used to monitor the patient's EEG as the TMS is applied and this may be used to determine when the patient's EEG has reached the normal or desired state. The operator can stop the TMS procedure when the patient's EEG is in the desired state.

In accordance with another aspect of the invention, the parameters of the TMS procedure can be adjusted depending upon the induced EEG that is displayed on display 42. For example, the strength of the magnetic field being applied, the frequency of the magnetic pulses, and the location of the TMS coil on the patient's head can be adjusted in response to the changes induced in the EEG as a result of a TMS procedure. The placement of TMS coil 28 can be adjusted by an operator holding the coil or, alternatively, robotic arm 35 can be used to hold TMS coil 28 on the patient's head. The operator, using control system 32, provides a signal on cable 36 to TMS control unit 26. TMS control unit 26 provides a signal on cable 31 to robotic arm control unit 33 that then moves robotic arm 35 so as to position TMS coil 28 at different locations on the patient's head.

Figure 2A:
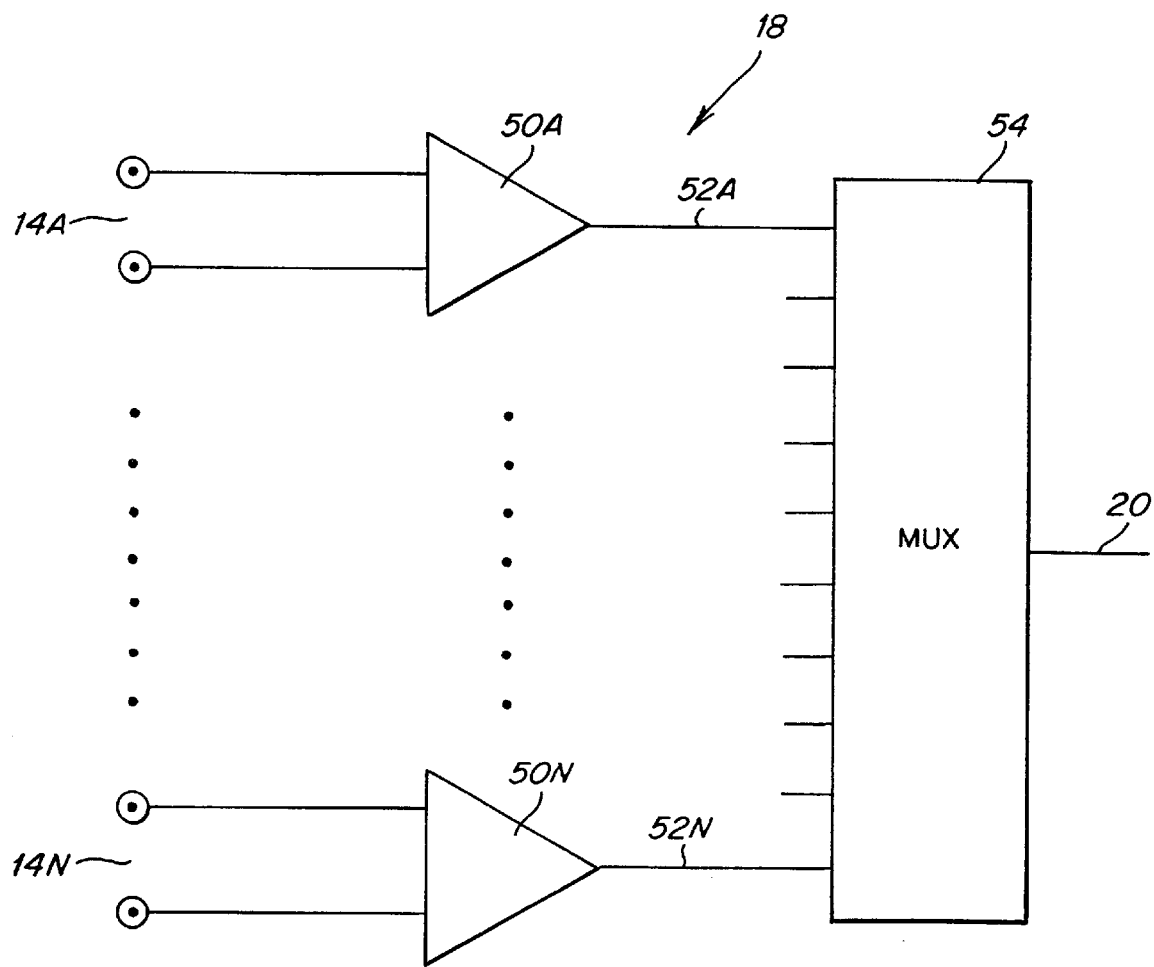
FIG. 2A is a block diagram of an amplifier that may be used in the EEG system illustrated in FIG. 1.

Reference is now made to FIG. 2A which figure illustrates a general embodiment of preamplifier 18 illustrated in FIG. 1. Preamplifier 18 includes a number of differential amplifiers 50a–50n with one differential amplifier provided for each electrode 14a–14n. The outputs 52a–52n are provided to a multiplexer 54. In response to control signals generated by EEG control unit 22, multiplexer 54 selects a particular output channel whose signal is then sent to EEG control unit 22 and on to control system 32.

As noted previously, differential amplifiers used in conventional EEG systems saturate upon exposure to the magnetic field generated by TMS coil 28. We have noted experimentally that the differential amplifiers corresponding to channels whose electrodes are closest to the source of the TMS pulse tend to become most saturated and tend to take the longest time to recover.

Figure 2B:
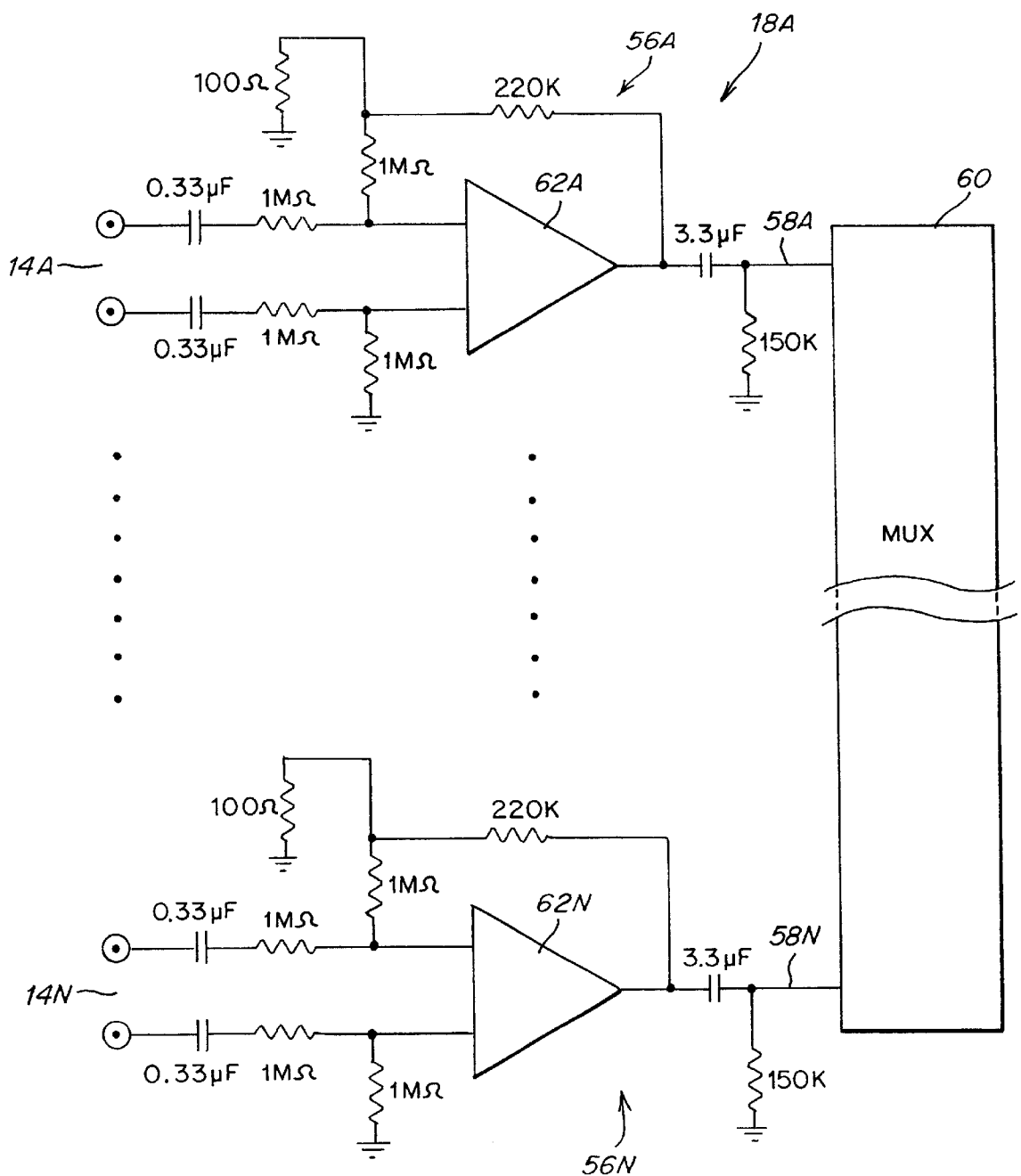
FIG. 2B is a more detailed schematic diagram of one embodiment of the amplifier illustrated in FIG. 2A.

FIG. 2B illustrates one specific example of a preamplifier that does not suffer from these drawbacks. Preamplifier 18a illustrated in FIG. 2B includes a number of differential amplifiers 56a–56n having outputs 58a–58n coupled to a multiplexer 60. Amplifier 62 used in preamplifier 18a may be a model number LT1079 amplifier available from Linear Technology. Multiplexer 60 may be a model number C04051 available from RCA or Motorola. In a preferred embodiment, these components are surface mount-type components.

When configured as illustrated in FIG. 2B, preamplifier 18a has 1MΩ input impedance, a common mode rejection ratio of 80 db, a gain of 2,200, a bandpass of 0.5 Hz to 70 Hz, and a noise level of 2–3 microvolts peak to peak. Multiplexer 60 may be clocked so as to operate at a sample rate of approximately 200 samples per second per channel. As noted before, one embodiment of the invention uses an 18-channel preamplifier so that the output of preamplifier 18a is an 18-channel analog multiplexed signal. A synchronization signal may be provided that permits identification of channel number 1. We have also found that locating preamplifier 18a so that it connects directly into the electrode harness provides improved performance.

When system 10 illustrated in FIG. 1 is used in conjunction with preamplifier 18a illustrated in FIG. 2B, the preamplifier does saturate upon application of a TMS pulse. However, preamplifier 18a is able to return to normal operation within no more than 20 milliseconds after the TMS pulse has been terminated. In a typical TMS procedure having a 10 Hz repetition rate, the time between TMS pulses is on the order of 100 milliseconds. Thus, the amplifier is able to come out of saturation and return to normal operation in no more than 20 milliseconds after cessation of the TMS pulse, thus providing at least 80 milliseconds of EEG data before a subsequent TMS pulse. Thus, the system of FIGS. 1 and 2B is able to provide a substantially complete EEG during a TMS procedure except for a relatively small time period during the application of the TMS pulse. It should be noted that this advantage is achieved without the need for any additional synchronization or timing control between the application of the TMS pulse and the operation of the EEG system. Thus, the present invention, in all embodiments, is advantageous because during a TMS procedure, the EEG system can simply be left on and the TMS pulses can be applied in any random manner.

Figure 2C:
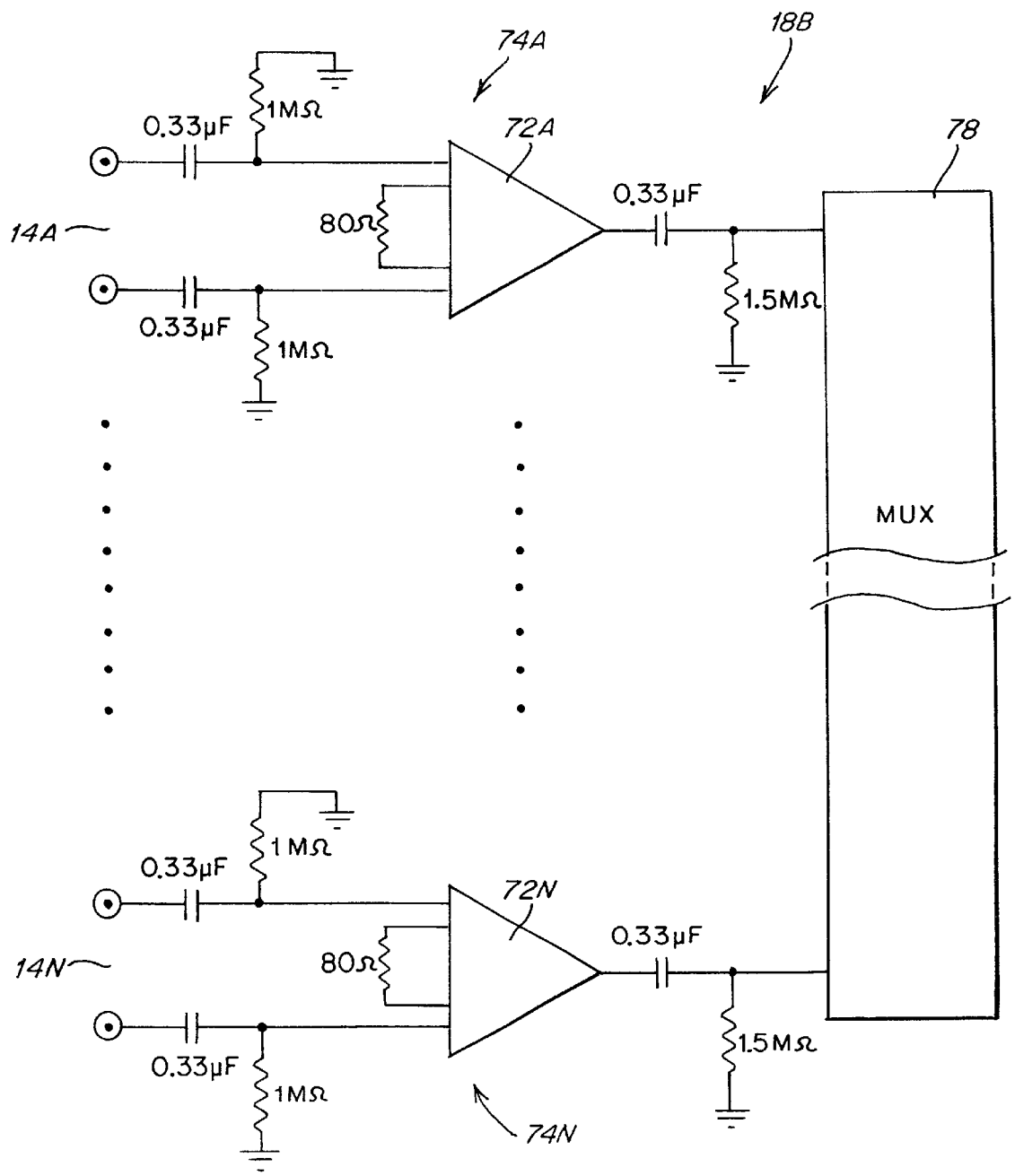
FIG. 2C is a more detailed schematic diagram of another embodiment of the amplifier illustrated in FIG. 2A.

Reference is now made to FIG. 2C, which figure illustrates another embodiment of preamplifier 18. In preamplifier 18b, amplifier 74 may be a model number INA126 available from Burr Brown. Multiplexer 78 may be a MAX4051 available from Maxim. As with other embodiments of preamplifier 18, the use of surface mount technology enhances performance. When configured as illustrated in FIG. 2C, preamplifier 18b has an input impedance of 1MΩ, common mode rejection ratio of 90 db, a gain of 1,000, a bandpass of 0.5 Hz to 900 Hz, and a noise level of 0.7 microvolts peak to peak. In the same manner as preamplifier 18a, multiplexer 78 can be clocked to provide 200 samples per second per channel and can provide a synchronization signal that permits identification of channel number 1.

Figure 3A:
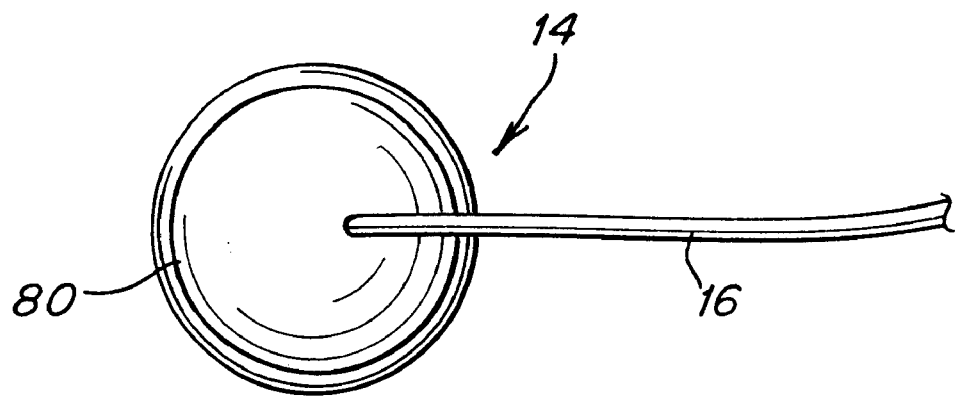
FIG. 3A is a plan view of an EEG electrode system in accordance with the present invention.
Figure 3B:
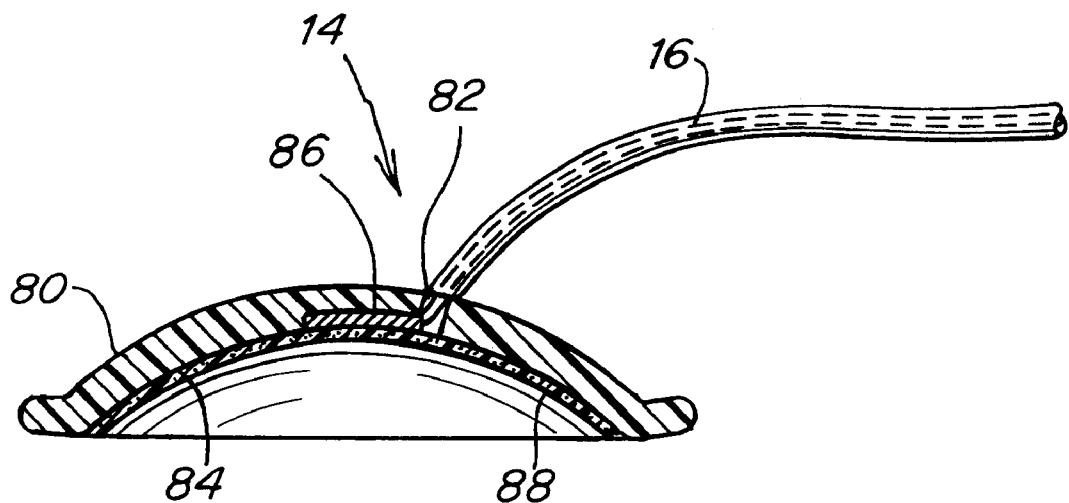
FIG. 3B is a cross-sectional view of the electrode system illustrated in FIG. 3A.

Reference is now made to FIGS. 3A and 3B, which figures illustrate one embodiment of electrode 14. As noted previously, the use of metal electrodes for detecting brain wave activity during TMS treatments is undesirable, since the eddy currents induced in the metal electrodes by the TMS pulses can cause burning of the patient's scalp due to heating of the electrodes. To overcome this problem, electrode 14 uses a conductive plastic electrode cup 80 available from, for example, Plastic One. A hole 82 is provided in the side of cup 80 to permit a tinseled Teflon insulated electrode wire (for example, standard Grass electrode wire) to be inserted. The end of the wire is stripped and tinned and this end is molded into the internal surface 84 in region 86 of cup 80. To reduce the impedance so that cup 14 is equivalent to the impedance of a typical metal electrode, a coat of conductive epoxy such as silver epoxy available from Circuit Works, model CW2400, is provided on the internal surface 84 of cup 80. Preferably, this conductive epoxy is applied over the entire internal surface 84 of cup 80.

The other end of wire 16 is collected together with wires from other electrodes and connected to preamplifier 18.

Electrode 14 thus provides the same performance as conventional metal electrodes but, since it is non-metallic, significantly reduces any risk of burns to the patient due to heating of the electrode. This can allow the present invention to use longer TMS pulses and longer pulse trains than in conventional TMS procedures.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended as limiting. The invention is limited only as defined in the following claims and the equivalents thereto.

What is claimed is:

1. A system for monitoring an electroencephalogram of a patient during administration of transcranial magnetic stimulation, comprising:

a transcranial magnetic stimulation (TMS) system to provide a train of pulses of magnetic energy, the train of pulses having a frequency;

an electroencephalogram (EEG) monitoring system to monitor electrical signals, wherein the electrical signals include electrical signals having a same frequency as the frequency of the train of pulses; and a control system, coupled between the EEG system and the TMS system, that responds to the electrical signals provided by the EEG system and controls the TMS system;

wherein timing of operation of the EEG system does not need to be synchronized to timing of operation of the TMS system.

2. The system of claim 1, wherein the control system monitors the electrical signals provided by the EEG system during the operation of the TMS system and stops the operation of the TMS system if the EEG signals are in a desirable state.

3. The system of claim 1, wherein the EEG system includes:
   a plurality of electrodes that are used to obtain signals from a patient; and
   a plurality of amplifiers, each amplifier in the plurality of amplifiers being coupled to a respective electrode in the plurality of electrodes, and wherein each amplifier has an output that saturates during a respective TMS pulse in the train of pulses and that returns to normal operation within 20 milliseconds after the respective TMS pulse ceases.

4. The system of claim 3, further comprising a multiplexer coupled to each output of each amplifier.

5. The system of claim 3, wherein the electrodes are electrically conductive plastic.

6. The system of claim 5, wherein the electrically conductive plastic electrodes include a coating of electrically conductive epoxy.

7. The system of claim 3, wherein each amplifier in the plurality of amplifiers has a passband of approximately 0.5 Hz to 70 Hz.

8. The system of claim 3, wherein each amplifier in the plurality of amplifiers has a passband of approximately 0.5 Hz to 900 Hz.

9. The system of claim 1, wherein the TMS system includes:
   a coil of wire; and
   a robotic arm, operatively coupled to the coil of wire and the control system, to movably position the coil of wire in one of a plurality of different locations.

10. The system of claim 1, wherein the control system monitors the electrical signals provided by the EEG system during the operation of the TMS system and automatically stops the operation of the TMS system if the EEG signals are in a desirable state.

11. The system of claim 1, wherein the control system monitors the electrical signals provided by the EEG system during the operation of the TMS system and automatically stops the operation of the TMS system if the EEG signals are in an undesirable state.

12. A method for controlling administration of transcranial magnetic stimulation to a patient, the method comprising the steps of:
   applying transcranial magnetic stimulation (TMS) to a patient;
   monitoring an electroencephalogram (EEG) of the patient during TMS using an EEG system that includes an amplifier that saturates during a TMS pulse and that returns to normal operation within 20 milliseconds after the TMS pulse is over; and
   stopping transcranial magnetic stimulation if the EEG of the patient indicates onset of a seizure.

13. The method of claim 12, further comprising the step of monitoring the EEG of the patient and continuing applying TMS until the EEG of the patient is in a desired state.

14. The method of claim 13, further comprising the step of monitoring the EEG of the patient and continuing applying TMS until the EEG of the patient is no longer in an undesired state.

15. The method of claim 12, wherein the TMS system includes a coil of wire that is operatively coupled to a robotic arm, the method further comprising a step of:
   remotely positioning the robotic arm to change a position of the coil of wire.

* * * * *